(12) United States Patent
Rosene et al.

(10) Patent No.: US 11,278,343 B2
(45) Date of Patent: Mar. 22, 2022

(54) VEHICLE SUSPENSION WITH COMMON HUB AND/OR KNUCKLE ASSEMBLY

(71) Applicant: WATSON & CHALIN MANUFACTURING, INC., McKinney, TX (US)

(72) Inventors: Nathan Rosene, Plano, TX (US); Chris Skarzenski, Dallas, TX (US); Walter O'Bannon, Allen, TX (US)

(73) Assignee: Watson & Chalin Manufacturing, Inc., McKinney, TX (US)

( * ) Notice: Subject to any disclaimer, the term of this patent is extended or adjusted under 35 U.S.C. 154(b) by 68 days.

(21) Appl. No.: 16/500,689

(22) PCT Filed: Apr. 19, 2018

(86) PCT No.: PCT/US2018/028379
§ 371 (c)(1),
(2) Date: Oct. 3, 2019

(87) PCT Pub. No.: WO2018/195320
PCT Pub. Date: Oct. 25, 2018

(65) Prior Publication Data
US 2020/0198426 A1    Jun. 25, 2020

Related U.S. Application Data

(60) Provisional application No. 62/487,767, filed on Apr. 20, 2017.

(51) Int. Cl.
*A61B 18/04*    (2006.01)
*H05H 1/24*    (2006.01)
(Continued)

(52) U.S. Cl.
CPC ............. *A61B 18/042* (2013.01); *B60G 7/001* (2013.01); *B60G 7/02* (2013.01); *B60T 1/06* (2013.01);
(Continued)

(58) Field of Classification Search
CPC ............ A61B 18/042; A61B 2090/373; A61B 2090/3735; A61B 2018/00291;
(Continued)

(56) References Cited

U.S. PATENT DOCUMENTS 1,442,944 A * 1/1923 Harvey .................... B60B 3/18
301/35.629
2,539,387 A * 1/1951 Alden .................... F16B 21/18
301/112

(Continued)

FOREIGN PATENT DOCUMENTS

EP        1276655 B1     9/2012
JP      2015223931 A    12/2015
(Continued)

OTHER PUBLICATIONS

Australian Examination Report dated May 20, 2020 for AU Patent Application No. 2018256422, 6 pages.
(Continued)

*Primary Examiner* — Darlene P Condra
(74) *Attorney, Agent, or Firm* — Smith IP Services, P.C.

(57) ABSTRACT

A vehicle suspension can include an adapter mounting face, a spindle rigidly mounted relative to the adapter mounting face, a wheel mounting hub including a hub body rotatably mounted on the spindle by bearings, and an adapter that spaces a brake component away from the adapter mounting face. Another vehicle suspension can include a spindle, bearings, and a wheel mounting hub rotatably mounted on the spindle by the bearings, the wheel mounting hub can
(Continued)

include a hub body and a wheel mounting flange, the hub body and the wheel mounting flange being separate components of the wheel mounting hub. A system for adapting a vehicle suspension to different suspension capacities can include multiple wheel mounting hubs including a same hub body internal configuration configured to be rotatably mounted on the spindle by the bearings, but the wheel mounting hubs including respective different wheel mounting flanges.

18 Claims, 12 Drawing Sheets

(51) Int. Cl.

| | | |
|---|---|---|
| H05H 1/34 | (2006.01) | |
| H05H 1/02 | (2006.01) | |
| H05H 1/48 | (2006.01) | |
| H05H 1/46 | (2006.01) | |
| B60G 7/00 | (2006.01) | |
| B60G 7/02 | (2006.01) | |
| B60T 1/06 | (2006.01) | |
| A61N 1/40 | (2006.01) | |
| A61L 2/14 | (2006.01) | |
| A61B 90/00 | (2016.01) | |
| A61B 18/00 | (2006.01) | |
| B60B 27/02 | (2006.01) | |
| B62D 7/18 | (2006.01) | |

(52) U.S. Cl.
CPC ............ *H05H 1/02* (2013.01); *H05H 1/2406* (2013.01); *H05H 1/34* (2013.01); *H05H 1/46* (2013.01); *H05H 1/48* (2013.01); *A61B 2018/00291* (2013.01); *A61B 2090/373* (2016.02); *A61B 2090/3735* (2016.02); *A61B 2090/395* (2016.02); *A61B 2090/3933* (2016.02); *A61B 2218/007* (2013.01); *A61L 2/14* (2013.01); *A61N 1/40* (2013.01); *B60B 27/02* (2013.01); *B60G 2204/418* (2013.01); *B60G 2206/50* (2013.01); *B62D 7/18* (2013.01); *H05H 1/466* (2021.05); *H05H 1/475* (2021.05); *H05H 2245/30* (2021.05)

(58) Field of Classification Search
CPC ...... A61B 2090/3933; A61B 2218/007; A61B 2090/395; B60G 7/001; B60G 7/02; B60G 2204/418; B60G 2206/50; B60T 1/06; H05H 1/48; H05H 1/46; H05H 1/2406; H05H 1/34; H05H 1/02; B60B 27/02; B62D 7/18; A61N 1/40; A61L 2/14
See application file for complete search history.

(56) References Cited

U.S. PATENT DOCUMENTS

| | | | | |
|---|---|---|---|---|
| 3,580,369 | A * | 5/1971 | Heck | F16D 65/853 188/264 E |
| 4,585,276 | A * | 4/1986 | Tirheimer | B60B 11/06 301/128 |
| 5,431,485 | A * | 7/1995 | Hayashi | B60B 3/10 301/105.1 |
| 5,967,536 | A * | 10/1999 | Spivey | B60G 7/001 280/124.141 |
| 5,975,765 | A | 11/1999 | Kawamura | |
| 6,616,156 | B1 * | 9/2003 | Dudding | B62D 7/18 280/93.512 |
| 7,281,769 | B2 | 10/2007 | Pete et al. | |
| 8,777,241 | B1 | 7/2014 | Hamernik | |
| 2004/0150181 | A1 | 8/2004 | Gottschalk | |
| 2006/0207384 | A1 | 9/2006 | Hardy | |
| 2006/0220444 | A1 * | 10/2006 | Darnell | B60B 27/00 301/111.01 |
| 2006/0244236 | A1 | 11/2006 | Cortez et al. | |
| 2007/0076994 | A1 * | 4/2007 | Norimatsu | F16C 33/7896 384/486 |
| 2007/0138754 | A1 * | 6/2007 | Moreau | B62D 7/18 280/93.512 |
| 2007/0246997 | A1 * | 10/2007 | Jenkinson | B60B 3/16 301/105.1 |
| 2008/0084042 | A1 | 4/2008 | Dinakaran et al. | |
| 2009/0129715 | A1 * | 5/2009 | Fukumura | B60B 27/0042 384/537 |
| 2009/0236813 | A1 | 9/2009 | Reid | |
| 2009/0257698 | A1 * | 10/2009 | Aritake | F16C 33/7896 384/484 |
| 2010/0007198 | A1 * | 1/2010 | Armfield | B60B 35/003 301/132 |
| 2012/0181850 | A1 * | 7/2012 | Armfield | B60B 35/122 301/132 |
| 2017/0036693 | A1 * | 2/2017 | Reid | B62D 7/18 |
| 2017/0097040 | A1 * | 4/2017 | Schultz | F16C 33/22 |
| 2017/0174260 | A1 | 6/2017 | Gottschalk et al. | |
| 2019/0056005 | A1 * | 2/2019 | Hall | F16D 69/02 |
| 2020/0254814 | A1 * | 8/2020 | Tandog | B60B 27/026 |

FOREIGN PATENT DOCUMENTS

| | | |
|---|---|---|
| WO | 2012003848 A1 | 1/2012 |
| WO | 2015148485 A1 | 10/2015 |
| WO | 2015148485 A2 | 10/2015 |

OTHER PUBLICATIONS

International Search Report with Written Opinion dated Aug. 2, 2019 for PCT Patent Application No. PCT/US2018/028379, 15 pages.
Examination Report dated Aug. 20, 2020 for New Zealand patent application 757295, 4 pages.
Examination Report dated Aug. 27, 2020 for Indian patent application 201917041430, 6 pages.
Expert Report dated Sep. 9, 2020 for Chilean patent application 201902965, 12 pages.
English translation of Expert Report dated Sep. 9, 2020 for Chilean patent application 201902965, 11 pages.
Search Report dated Sep. 9, 2020 for Chilean patent application 201902965, 3 pages.
English translation of Search Report dated Sep. 9, 2020 for Chilean patent application 201902965, 2 pages.
Search Report dated Nov. 5, 2020 for Canadian patent application 3,056,799, 3 pages.
Examination Report dated Nov. 10, 2020 for New Zealand patent application 757295, 3 pages.
Search Report and Opinion dated Nov. 23, 2020 for European patent application 18787207.2, 7 pages.
Expert Response dated Dec. 31, 2020 for Chilean patent application 201902965, 9 pages.
English translation of Expert Response dated Dec. 31, 2020 for Chilean patent application 201902965, 8 pages.
Search Report dated Dec. 31, 2020 for Chilean patent application 201902965, 3 pages.
Examination Report dated Jul. 30, 2021 for Canadian patent application 3,056,799, 3 pages.
Examination Report dated Apr. 22, 2021 for EP Patent Application No. 18787207.2-1012, 4 pages.
CO Office Action dated May 3, 2021 for CO Patent Application No. NC2019/0011600, 7 pages.
Canadian Examiner's Report dated Nov. 19, 2021 for CA Patent Application No. 3,056,799, 3 pages.

* cited by examiner

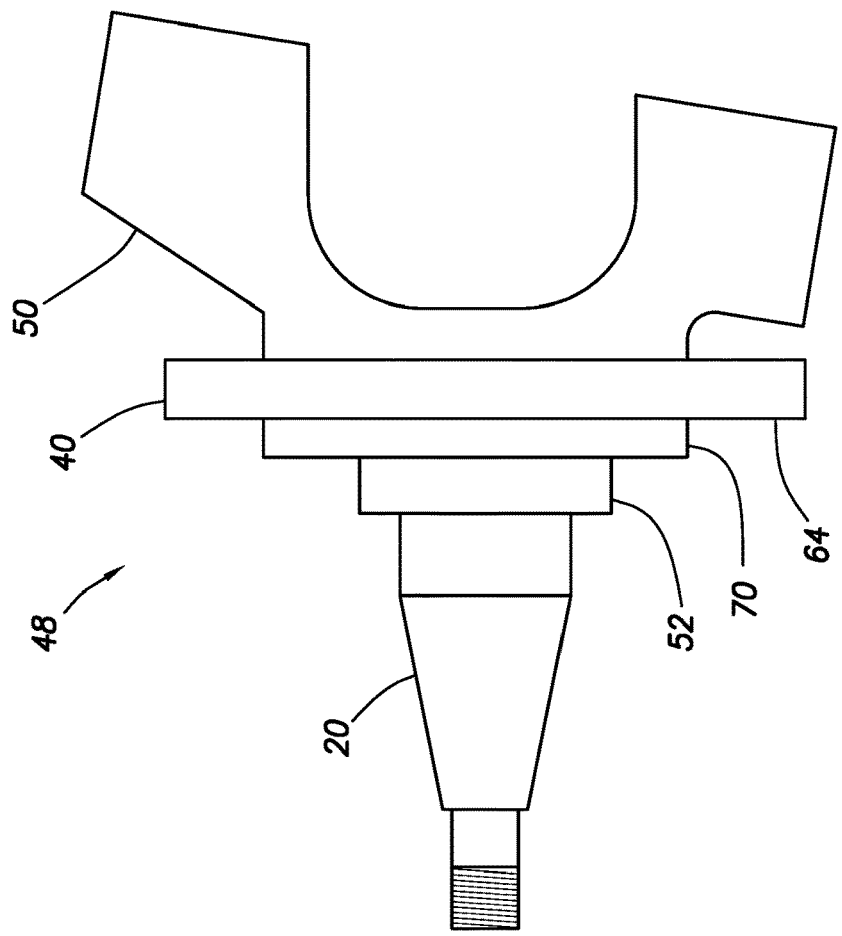
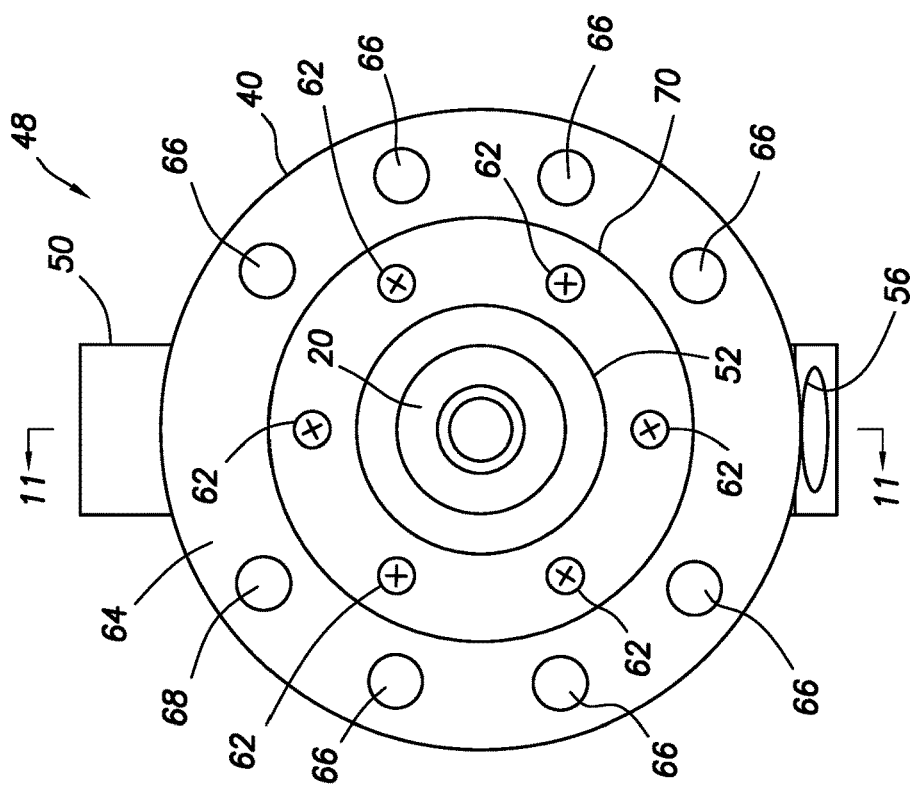
FIG.10
FIG.9

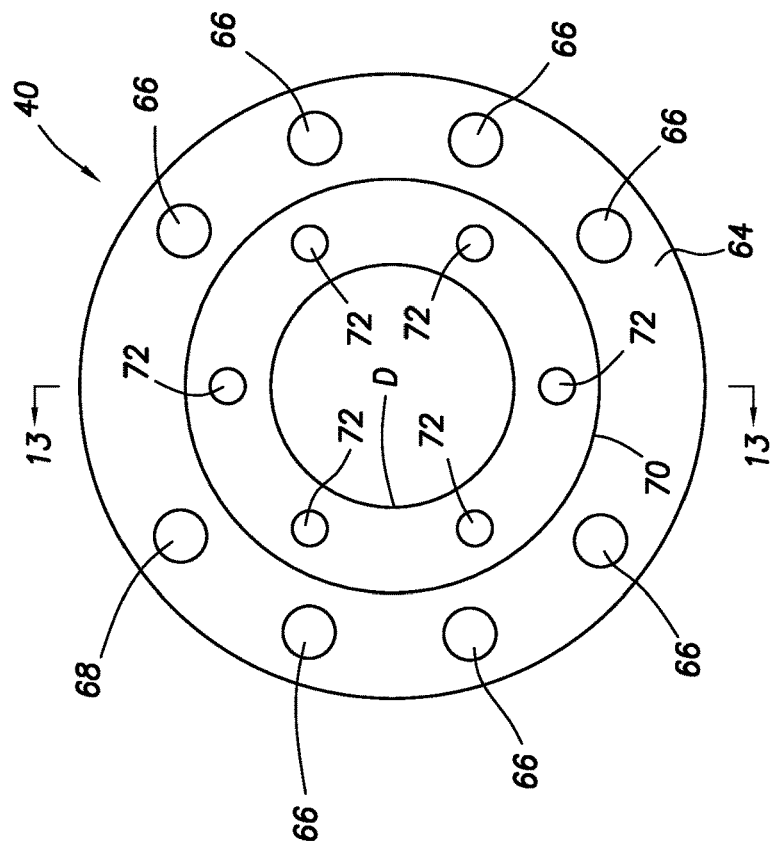
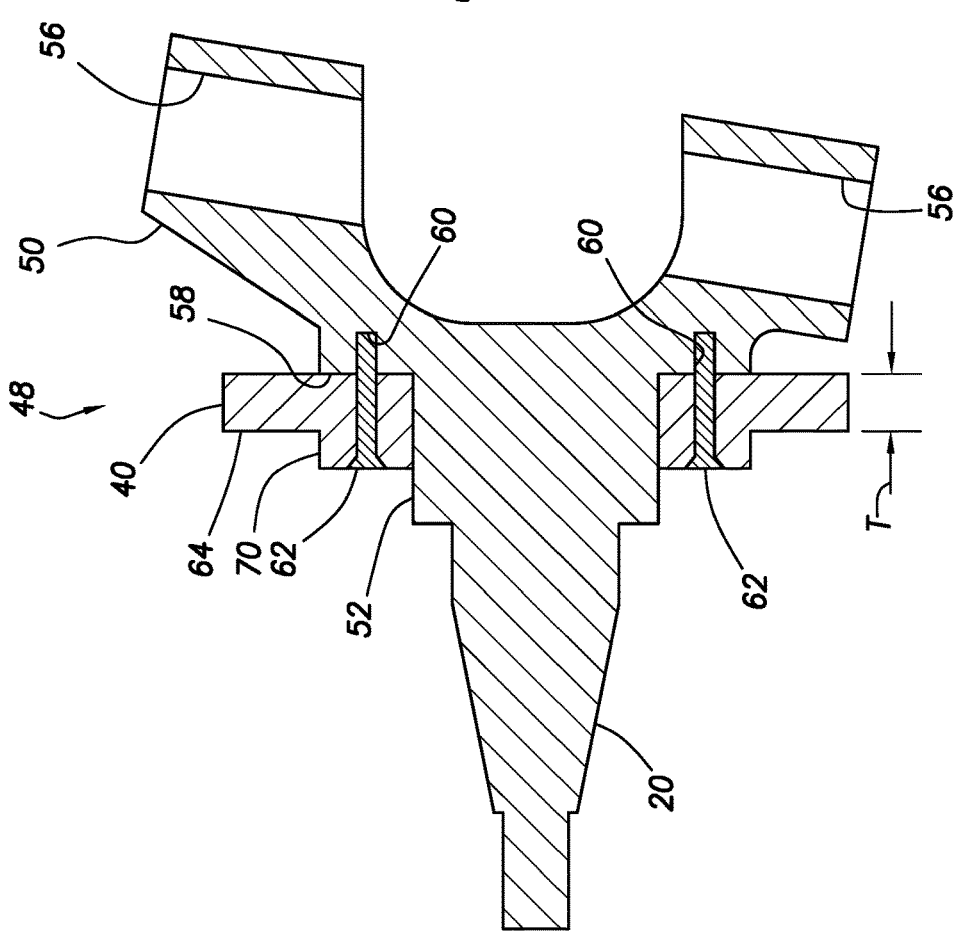

VEHICLE SUSPENSION WITH COMMON HUB AND/OR KNUCKLE ASSEMBLY

CROSS-REFERENCE TO RELATED APPLICATIONS

This application is a national stage under 35 USC 371 of International Application No. PCT/US18/28379 filed on 19 Apr. 2018, which claims priority to U.S. Provisional Application No. 62/487,767 filed on 20 Apr. 2017. The entire disclosures of these prior applications are incorporated herein by this reference.

TECHNICAL FIELD

This disclosure relates generally to vehicle suspensions and, in one example described below, more particularly provides for use of a common hub and/or knuckle assembly with various vehicle suspension capacities.

BACKGROUND

A wheel hub can be used to transfer loads from a rotating wheel into a spindle through connected bearings. It is typical for an axle of a specific capacity to use an industry standard spindle size, bearing size, hubcap size, and wheel mounting surface dimensions. These sizes all vary according to a weight capacity of the axle. That is, axles with different capacities typically have corresponding differently dimensioned spindles, bearings, hubcaps and wheel mounting surfaces.

In addition, different capacities of steerable axles traditionally use corresponding different knuckles, with the different knuckles having varying feature sizes. These feature sizes then affect various other wheel end components that interface with the knuckle. Additionally, some desired features of lower capacity axles may drive packaging constraints. This includes track and desired wheel mount face, wheel size with associated wheel stud pitch circle, and brake size.

It will be appreciated that improvements are continually needed in the arts of designing, manufacturing, assembling and maintaining vehicle suspensions. The present disclosure provides such improvements to the arts for use with a variety of different vehicle suspension types, such as, steerable and non-steerable, different axle types and capacities, etc.

BRIEF DESCRIPTION OF THE DRAWINGS

FIGS. 9-11 are representative side, rear and cross-sectional views of the steering knuckle with another example of the brake component mounting adapter.

FIGS. 12 & 13 are representative side and cross-sectional views of the adapter, with FIG. 13 being taken along line 13-13 of FIG. 12.

DETAILED DESCRIPTION

Figure 1:
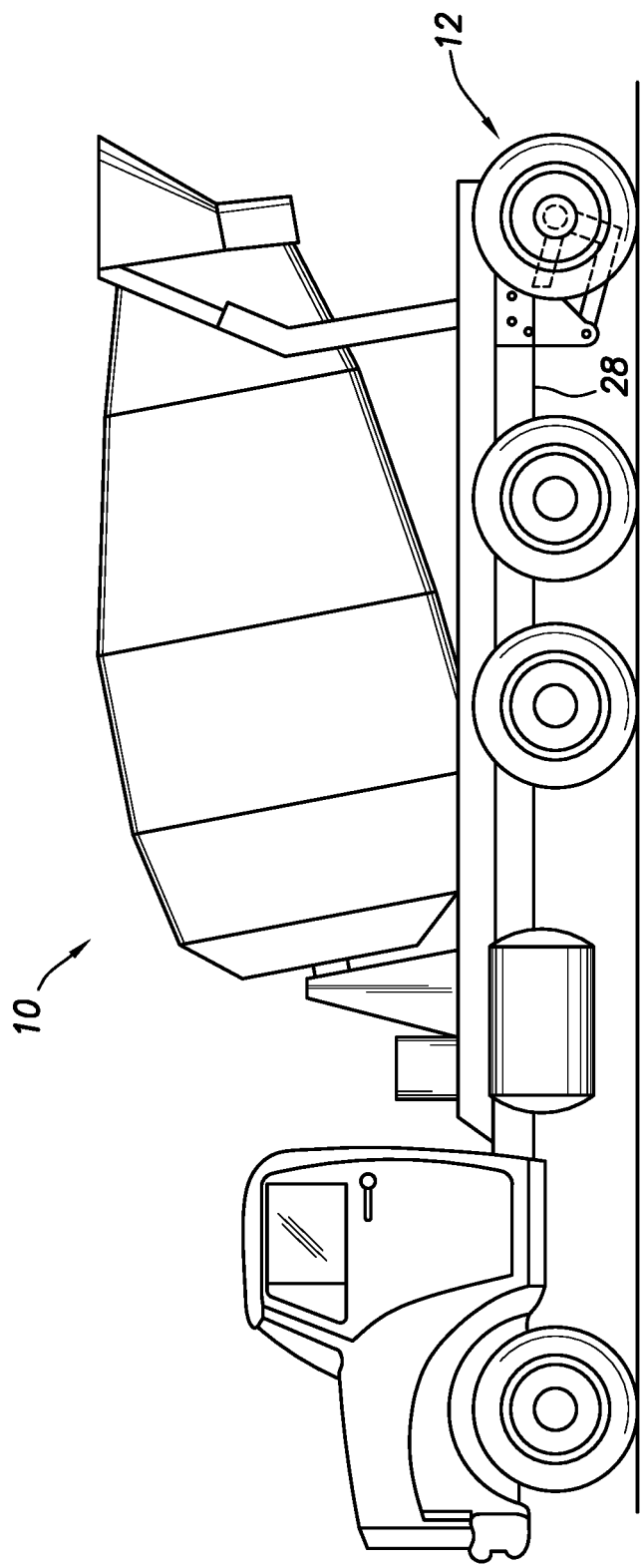
FIG. 1 is a representative side view of an example of a vehicle which can embody principles of this disclosure.

Representatively illustrated in accompanying drawings is a vehicle suspension, including components thereof, and an associated method, which can embody principles of this disclosure. However, it should be clearly understood that the vehicle suspension and method are merely one example of an application of the principles of this disclosure in practice, and a wide variety of other examples are possible. Therefore, the scope of this disclosure is not limited at all to the details of the vehicle suspension and method described herein and/or depicted in the drawings.

Representatively illustrated in FIG. 1 is a vehicle 10. The vehicle 10 in this example is a cement transport truck, but other types of vehicles (such as, passenger vehicles, buses, tractors, trailers, etc.) may incorporate the principles of this disclosure.

The vehicle 10 depicted in FIG. 1 includes a steerable auxiliary suspension 12. In this example, the suspension 12 is lowered into contact with a road surface when desired to distribute a load carried by the vehicle 10 over more axles, comply with bridge laws, etc. However, the scope of this disclosure is not limited to use with steerable auxiliary suspensions.

The FIG. 1 suspension 12 is attached to a longitudinally extending frame 28 of the vehicle 10. In other examples, the suspension 12 could be attached to a body, combined body and chassis, or another component or combination of vehicle components. Thus, the scope of this disclosure is not limited to any particular details of the vehicle 10 or the suspension 12 as depicted in FIG. 1 or as described herein.

Common Hub

Instead of requiring a different hub for each different suspension capacity, examples described herein can standardize spindle diameter, bearing inner and outer diameter, and hubcap across a variety of different suspension capacities. The examples described herein are used for auxiliary steerable axle configurations, but other axle configurations could also benefit from the improvements described herein. For example, other applications could include commercial truck and trailer axles, passenger vehicles, and vocational truck and trailer axles.

The common hub designs described herein reduce complexity and allow for more flexible and modular configurations. Axles and spindles can remain dimensionally identical for different suspension capacities. The wheel end components (e.g., a brake drum, wheel, etc.) for different suspension capacities are interchangeable onto a common spindle and bearing.

In specific examples described herein, three different suspension capacities can be standardized, so that they use the same spindle and bearings. The examples include 8,000 lb (8 k, or ~3600 kg), 10,000 lb (10 k, or ~4500 kg), and 13,000 lb (13 k, or ~5900 kg) capacity axles. These are currently the three most common axle capacities offered in the US auxiliary lift axle market. Other suspension capacities may be used, within the scope of this disclosure.

In these examples, a standard "FF" type spindle as classified by the Society of Automotive Engineers (SAE) and mating bearing is used for all three capacities. The fitment to different brakes and wheels/tires can be achieved by the use of a uniquely configured hub.

Two example designs for this hub described herein are: one-piece and two-piece. Both designs can be comprised of (but not limited to) a cast metal alloy, such as ductile iron or aluminum. A main body of the hub can accommodate industry standard "FF" type bearings and hubcap for fitment to an "FF" type spindle.

Two configurations of the one-piece hub example are described herein—one of each for use with an 8 k and 10 k wheel stud hole pattern on a wheel mounting flange. In the described examples, this wheel mounting flange and hole pattern is cast into a main shape of the hub body.

For the two-piece hub example, all configurations can share a same common hub body containing the "FF" type bearings. A removable wheel mounting flange or body can be attached to the hub body by the use of fasteners in combination with a splined mating surface between the two components to ensure alignment.

Figure 2:
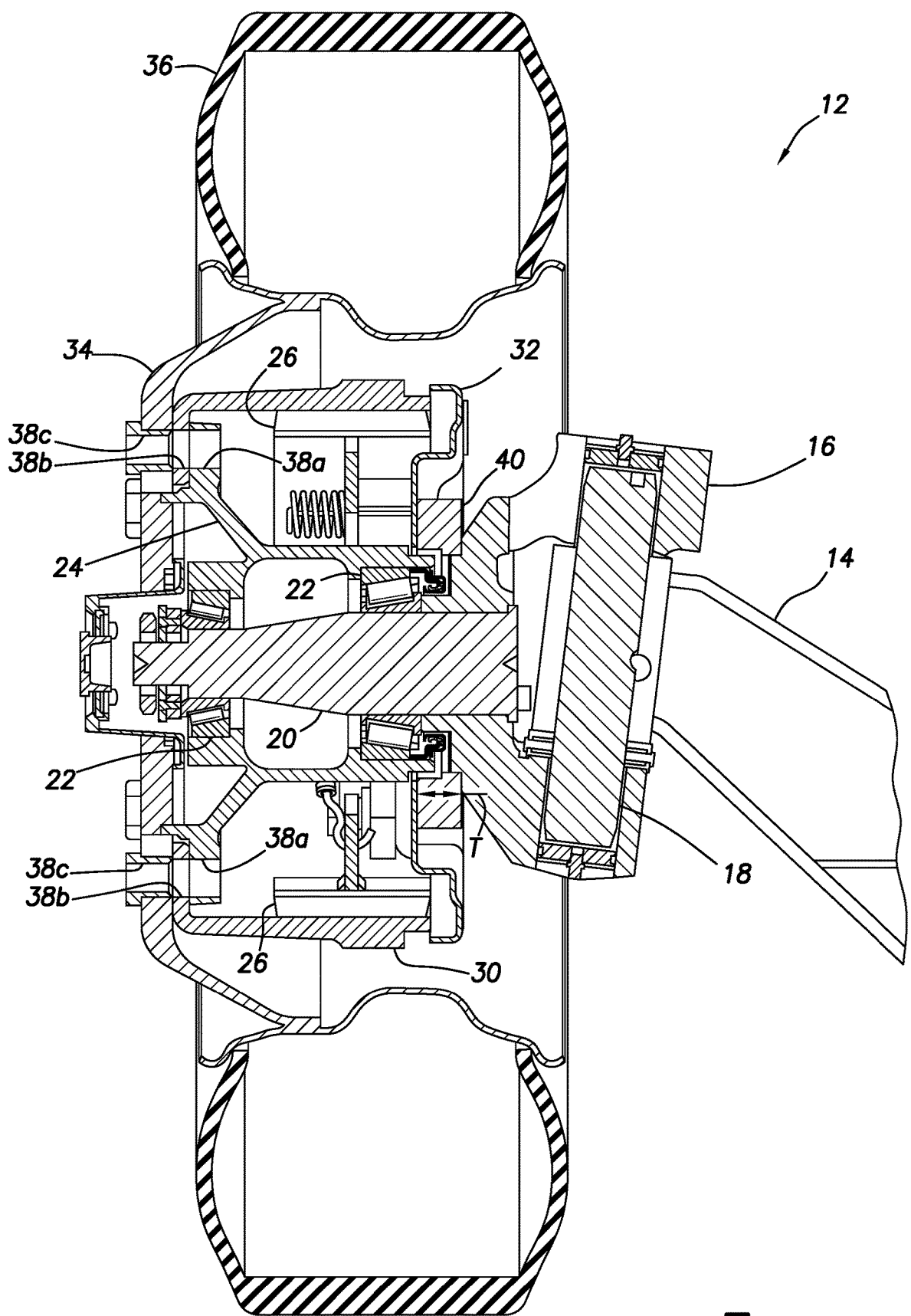
FIGS. 2 & 3 are representative partially cross-sectional views of an example of a vehicle suspension that may be used with the vehicle of FIG. 1, and which can incorporate the principles of this disclosure.
Figure 3:
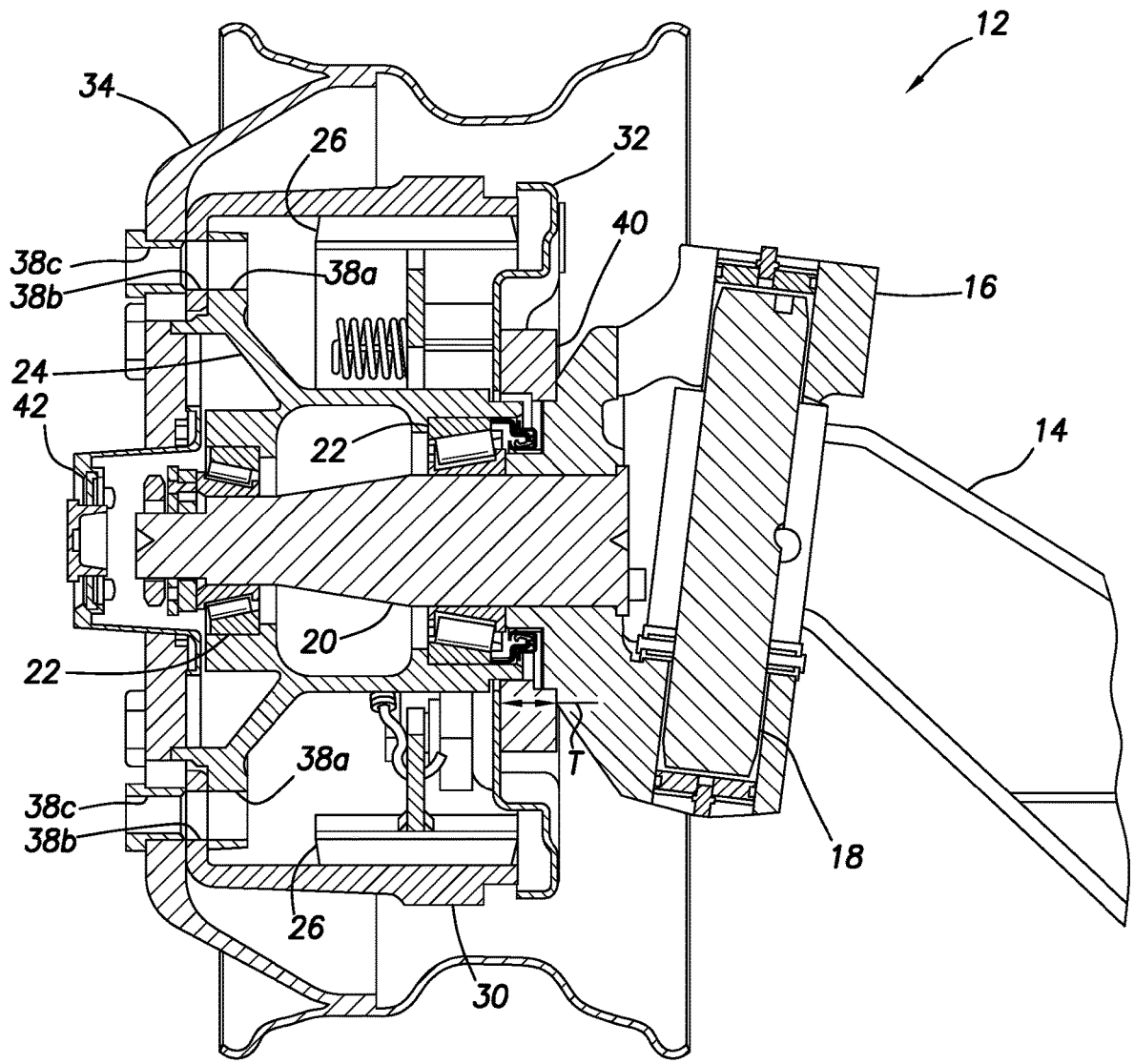

Referring additionally now to FIGS. 2 & 3, a portion of the suspension 12 is representatively illustrated. The suspension 12 may be used with the vehicle 10 of FIG. 1, or it may be used with other suspensions.

As depicted in FIGS. 2 & 3, the suspension 12 includes an axle 14, a knuckle 16, a king pin 18, a spindle 20, bearings 22, a wheel mounting hub 24, brake shoes 26, a brake drum 30 and a brake backing plate 32. A wheel 34 and a tire 36 are mounted to the hub 24 using conventional wheel studs (not shown) that extend through aligned holes 38a-c in the hub 24, brake drum 30 and wheel 34.

As mentioned above, the spindle 20 and bearings 22 in this example are industry standard "FF" type. However, other types may be used in keeping with the scope of this disclosure.

An adapter 40 spaces the brake mounting plate 32 (and, thus, the brake shoes 26 and various other brake components) an appropriate distance away from the knuckle 16. The adapter 40 can be provided with a variety of different lateral thicknesses T to accommodate various different brake dimensions corresponding to different suspension capacities.

For example, an 8 k suspension will have different brake shoe 26 and brake drum 30 sizes, as compared to a 10 k suspension. For one or more suspension capacities (such as, a 13 k suspension), the adapter 40 may not be used, or may have a minimal thickness T.

Figure 4A:
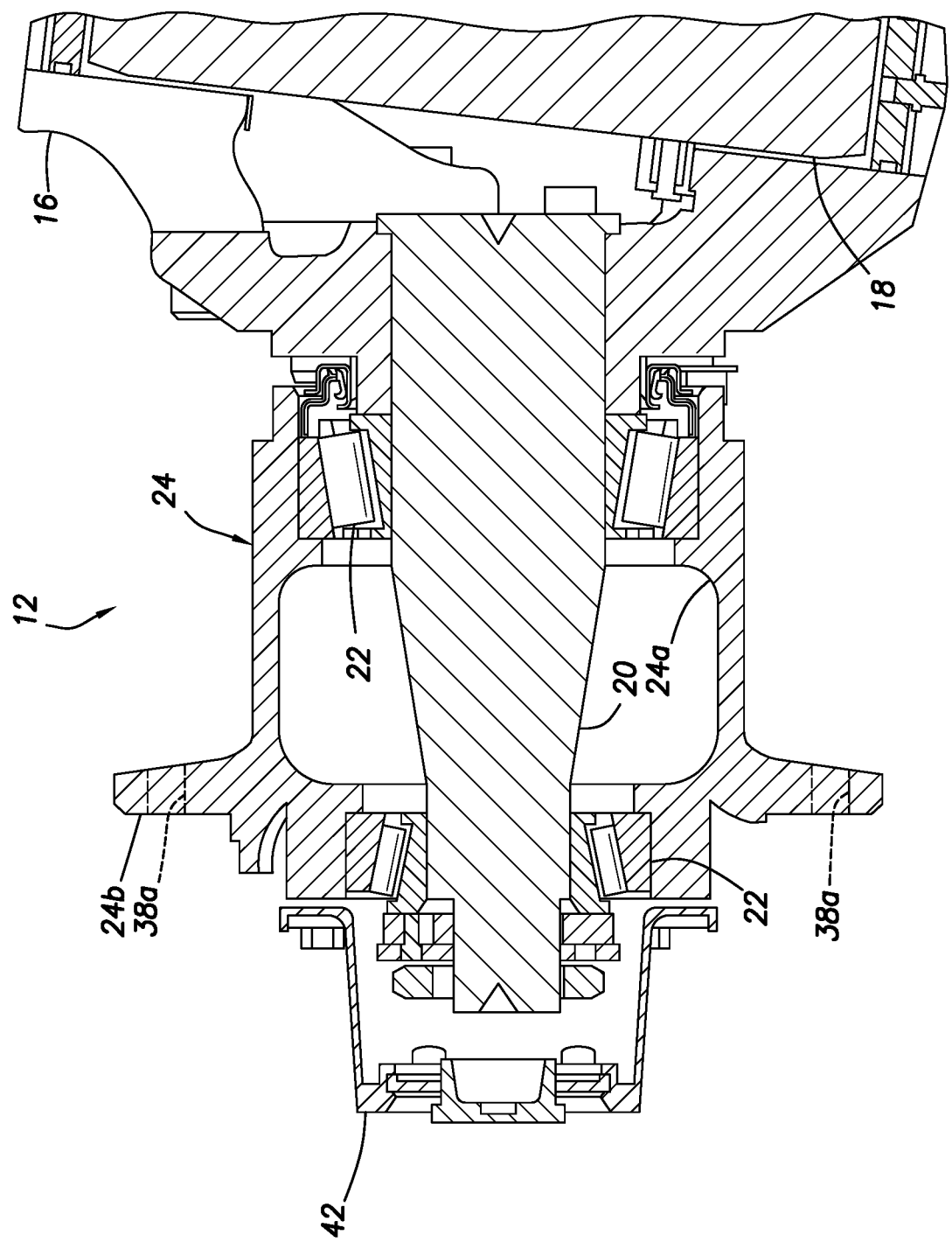
FIGS. 4A & B are representative cross-sectional views of a portion of the vehicle suspension, with different wheel mounting hub configurations.

Referring additionally now to FIGS. 4A & B, additional examples of the suspension 12 are representatively illustrated, without the brake components, wheel or tire. In FIG. 4A, an 8 k capacity version of the suspension 12 is depicted, and in FIG. 4B, a 10 k capacity version of the suspension is depicted. The hub 24 is a single integral component in the FIGS. 4A & B examples.

Note that the same spindle 20, bearings 22 and hub cap 42 are used with both of the 8 k and 10 k capacity versions of the suspension 12. A body 24a of the hub 24 is the same in FIGS. 4A & B, so that the interfaces between the hub and each of the spindle 20, bearings 22 and hub cap 42 are the same for both of the 8 k and 10 k capacity versions of the suspension 12. Thus, the same hub body 24a configuration (e.g., at interfaces between the hub body 24a, the spindle 20 and the bearings 22) can be used, even though the suspension capacities are different.

However, note that a wheel mounting flange 24b is not the same in FIGS. 4A & B. The flange 24b in the 8 k capacity version of the suspension 12 is different from the wheel mounting flange in the 10 k capacity version. Thus, a different hub 24 is used for each of the different capacities, although the hub body 24a internal configuration (e.g., at interfaces between the hub body 24a, the spindle 20 and the bearings 22) is the same.

Figure 5:
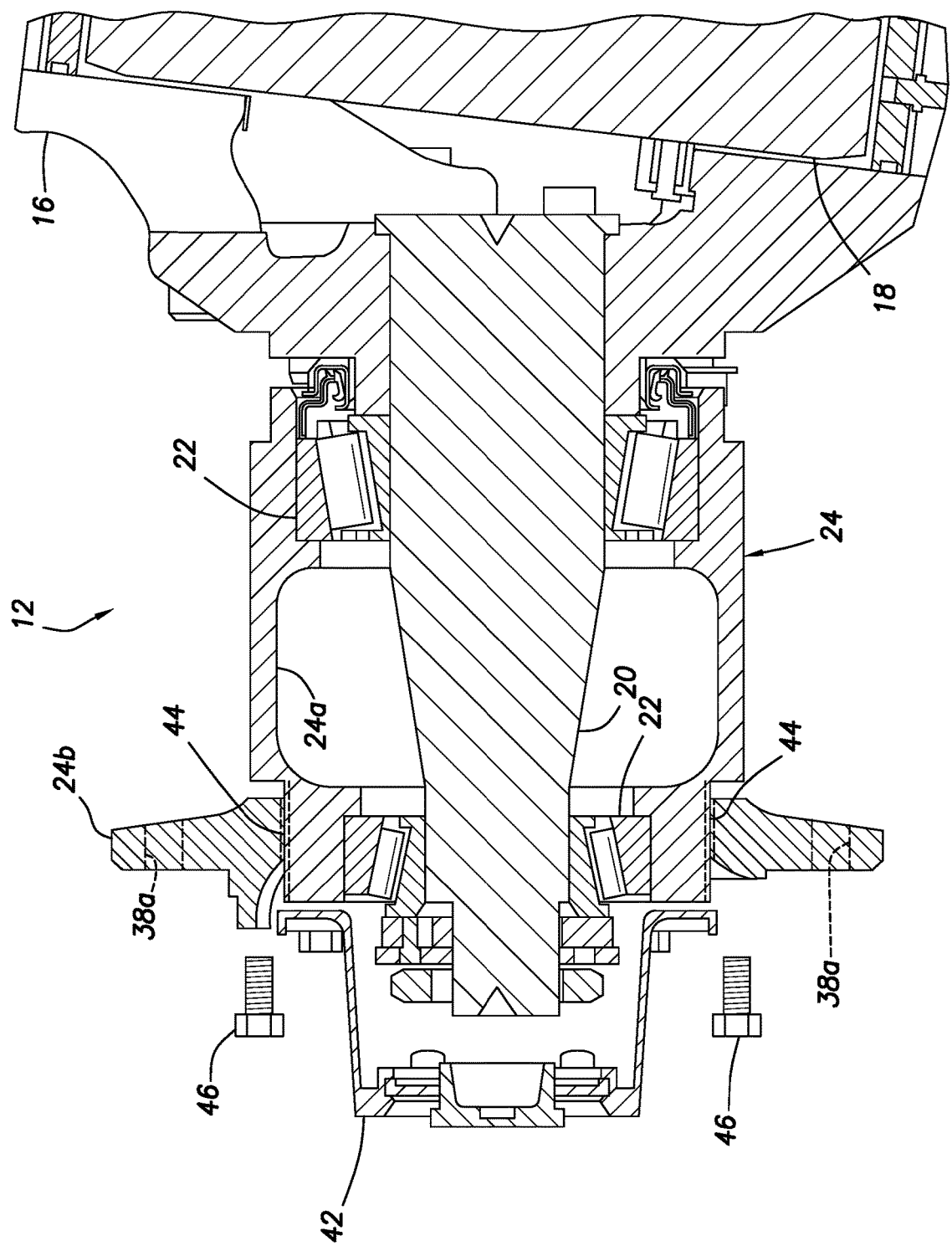
FIG. 5 is a representative cross-sectional view of another example of the vehicle suspension, with a two-piece wheel mounting hub.

Referring additionally now to FIG. 5, another example of the suspension 12 is representatively illustrated. In this example, the hub 24 is not a single integral component, but instead comprises a separate hub body 24a and wheel mounting flange 24b.

Splines 44 are used to rotationally secure the wheel mounting flange 24b to the body 24a. Fasteners 46 may also, or alternatively, be used to secure the flange 24b to the body 24a.

Figure 4B:
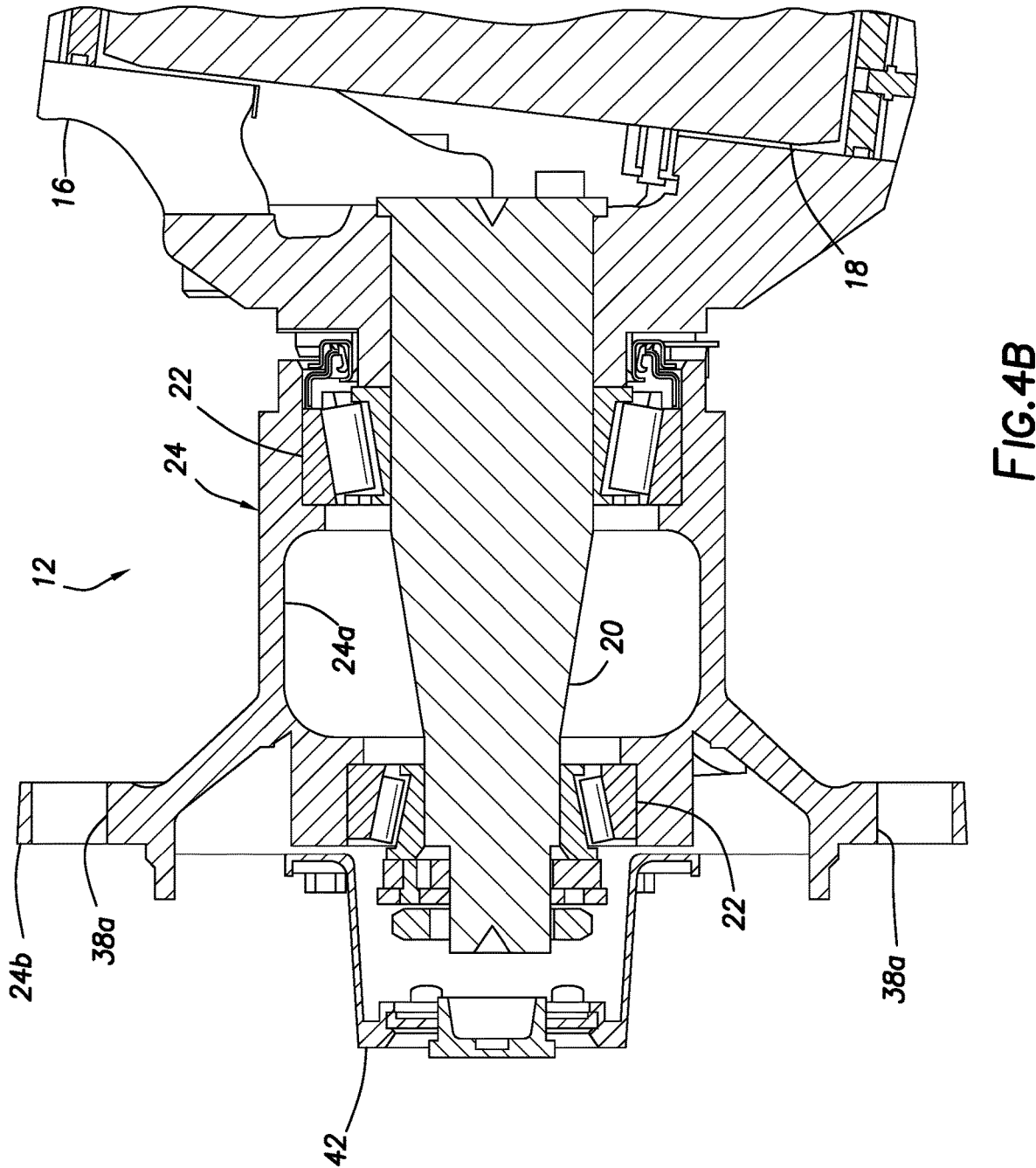

Note that the flange 24b as depicted in FIG. 5 is configured similar to the flange 24b in the 8 k capacity version of the suspension 12 depicted in FIG. 4A. Instead of this flange 24b, another flange configured similar to the flange in the 10 k capacity version of the suspension 12 as depicted in FIG. 4B could be secured to the hub body 24a to thereby provide for mounting a 10 k brake drum 30 (see FIG. 3). The wheel mounting flange 24b can be drilled to accommodate different numbers of wheel studs and/or different bolt circle diameters or pitches.

Thus, in the FIG. 5 example, the same hub body 24a can be used for different capacity versions of the suspension 12. Only the wheel mounting flange 24b is changed to adapt the hub 24 itself to a particular capacity version of the suspension 12. In addition, a different adapter 40 may be used to mount the corresponding different brake components for the respective different suspension capacities.

If disc brakes are used, a disc brake rotor could also be secured to the hub body 24a (such as, using splines). In some examples, the disc brake rotor and the wheel mounting flange 24b could be integrally formed as a single component that is secured to the hub body 24a with the splines 44.

Figure 6:
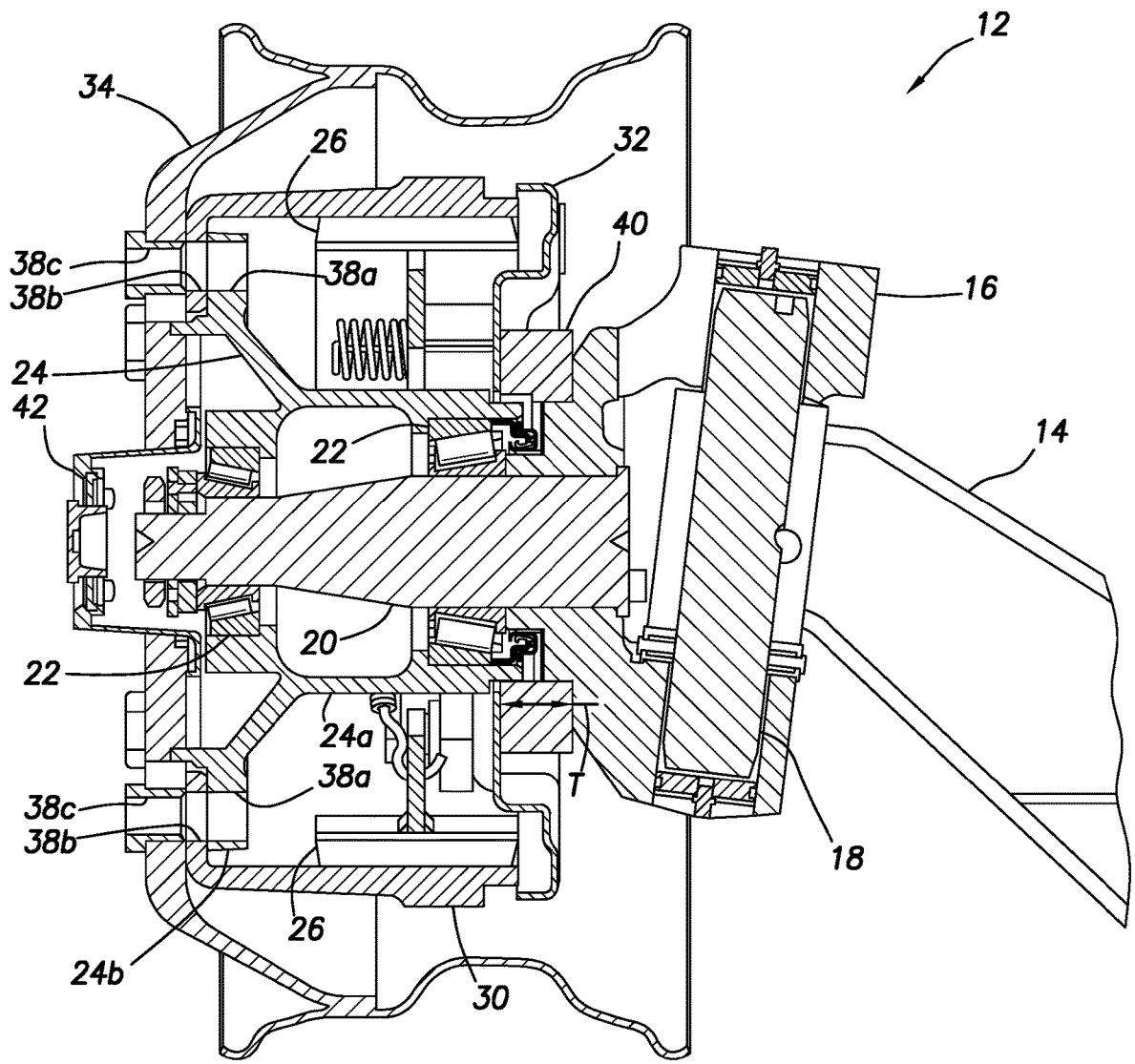
FIG. 6 is a representative cross-sectional view of another example of the vehicle suspension, with an increased thickness brake component mounting adapter.

Referring additionally now to FIG. 6, another configuration of the suspension 12 is representatively illustrated. In this configuration, the adapter 40 has an increased thickness T as compared to the adapter depicted in FIGS. 2 & 3.

This increased thickness T of the adapter 40 spaces the brake backing plate 32 and other brake components farther from the steering knuckle 16, to accommodate reduced widths of the brake shoes 26 and brake drum 30. Thus, the common hub body 24a can be used with the same spindle 20 and bearings 22, even though different brake components are used.

Other brake components that can be spaced apart from the steering knuckle with an adapter include a brake spider (similar to a cast backing plate), a torque plate (used with disc brakes) and brake shoes (for example, the adapter could provide a desired spacing between the brake shoes and a backing plate or brake spider). Note that a brake spider can be cast as an integral component of a steering knuckle.

Knuckle Assembly

In examples described herein, certain features of the steering knuckle 16 are standardized around those of the 13 k capacity, thereby increasing the component durability of the 8 k and 10 k capacity axles, while taking advantage of the economy of scale. At the same time, packaging constraints of the lower capacity interfacing components can be satisfied to enable a standardized 13 k steering knuckle to be used with 8 k and 10 k wheel end components.

Figure 8:
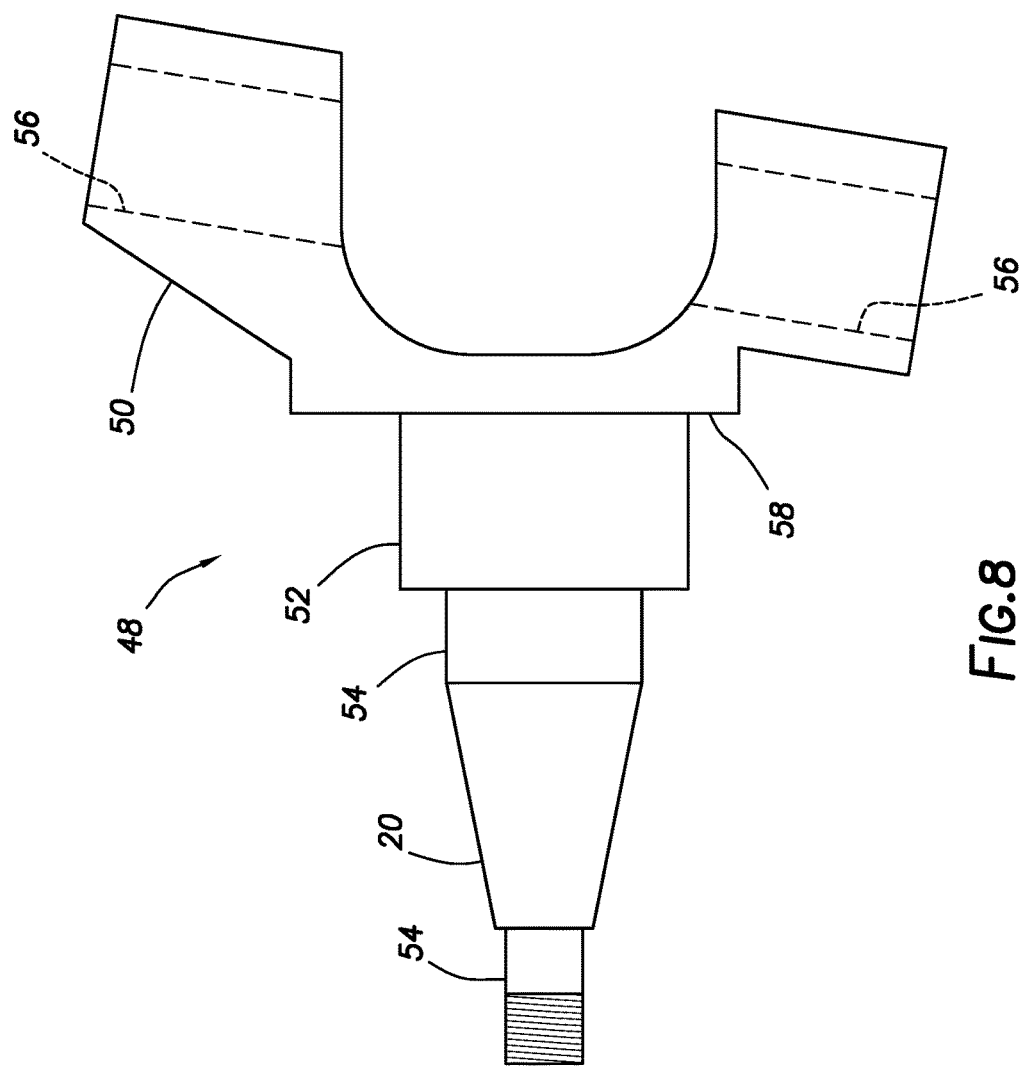
FIGS. 7 & 8 are representative side and rear views of a steering knuckle that may be used with the vehicle suspension.
Figure 7:
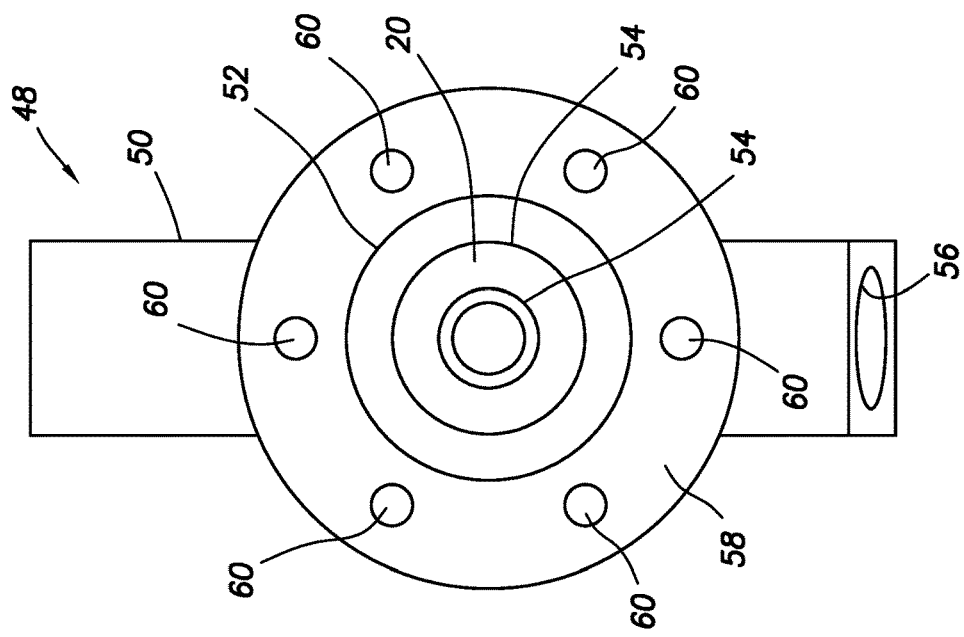

Referring additionally now to FIGS. 7 & 8, side views of an example of a steering knuckle assembly 48 are representatively illustrated. The steering knuckle assembly 48 may be used with the suspension 12 described above, or it may be used with other suspensions.

As depicted in FIGS. 7 & 8, the steering knuckle assembly 48 includes a knuckle backbone 50, a seal boss 52, the spindle 20 and bearing journals 54. The backbone 50 has bores 56 therein for receiving the king pin 18. The seal boss 52 is sealingly engaged by a seal pressed into the hub 24 (see FIG. 3). The bearing journals 54 support the bearings 22 (see FIG. 3).

In this example, an adapter mounting face 58 is formed on the backbone 50. Threaded holes 60 are machined into the mounting face 58 for securing the adapter 40 (see FIG. 6) to the backbone 50. The spindle 20 is rigidly mounted relative to the adapter mounting face 58 (for example, the spindle could be press-fit into the knuckle backbone 50, welded thereto, or integrally formed therewith).

Referring additionally now to FIGS. 9-11, side and cross-sectional views of the knuckle assembly 48 with another configuration of the adapter 40 are representatively illustrated. In this example, fasteners 62 are threaded into the holes 60 in the backbone 50 to secure the adapter 40 to the backbone.

The FIGS. 9-11 adapter 40 configuration includes a brake mounting face 64 and holes 66 for mounting brake components (such as, the brake backing plate 32) to the adapter 40. An anti-lock braking system (ABS) sensor mounting hole 68 can also be provided in the adapter 40. A brake pilot diameter 70 can be formed on the adapter 40 to engage the braking components and ensure that they are appropriately centered relative to the spindle 20.

The adapter 40 can be configured to interface with different brake geometries, so that the knuckle backbone 50 can be used with different suspension capacities. As mentioned above, a width or thickness of the adapter 40 can be changed to accommodate different brake components. In the FIGS. 9-11 examples, the brake mounting holes 66 (such as, a hole diameter and bolt circle diameter) may also, or alternatively, be changed to accommodate different brake components. Thus, the spindle 20, bearings 22 and hub body 24a can remain the same, even though the brake components vary between different suspension capacities.

Figure 13:
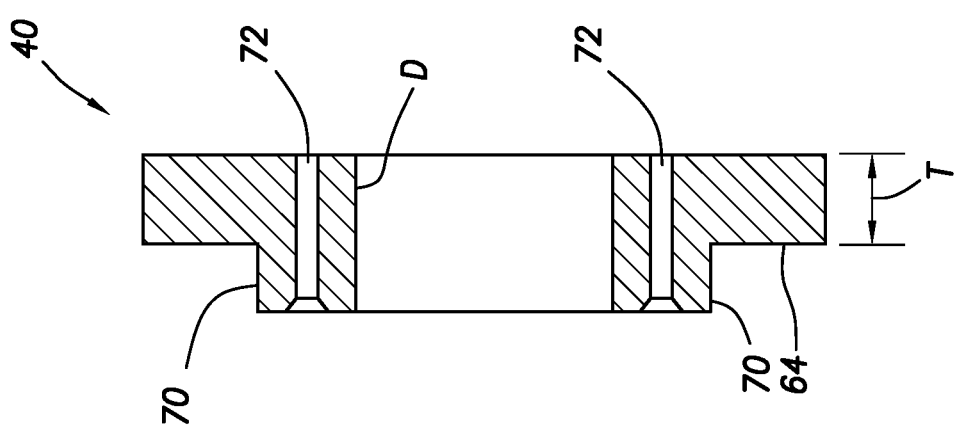

Referring additionally now to FIGS. 12 & 13, the adapter 40 is representatively illustrated in side and cross-sectional views. Note that the adapter 40 has holes 72 formed therethrough for the fasteners 62 to mount the adapter to the mounting face 58 on the backbone 50. An inner diameter D of the adapter 40 is sized to fit closely on the seal boss 52 (see FIG. 11).

Figure 14:
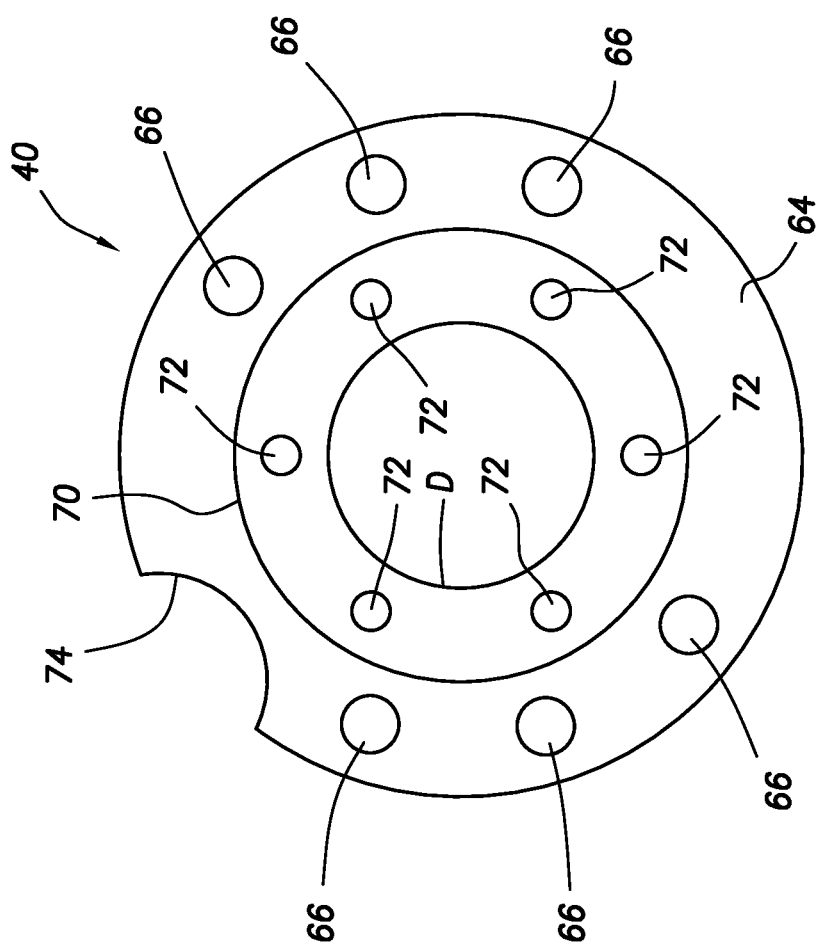
FIG. 14 is a representative side view of another example of the adapter.

Referring additionally now to FIG. 14, another configuration of the adapter 40 is representatively illustrated. In this example, a cutout 74 is provided to accommodate a brake cam (not shown) of the type well known to those skilled in the art. This configuration may be used with an 8 k capacity suspension.

In some examples, the separate adapter 40 may not be used, or the brake mounting face 64 could be integrally formed with the steering knuckle 16. In these examples, the cutout 74 could be formed in the steering knuckle 16 (e.g., in the brake mounting face 64, as part of a brake spider, or in a torque plate if disc brakes are used).

Figure 16:
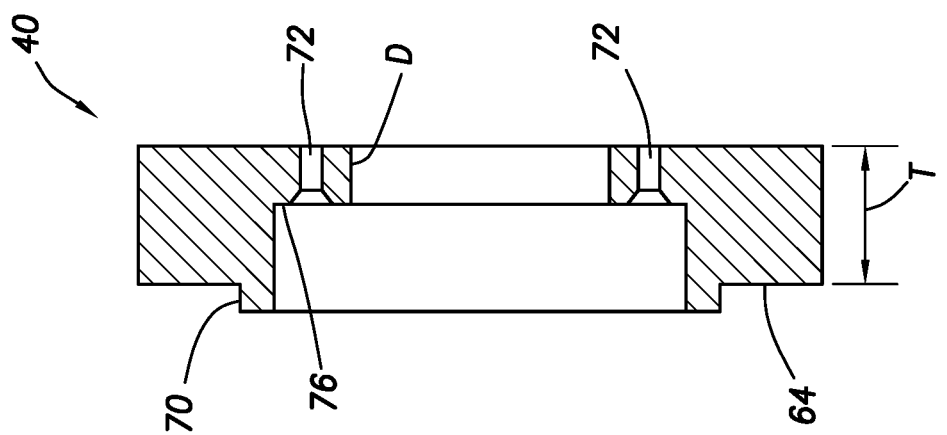
FIGS. 15 & 16 are representative side and cross-sectional views of another example of the adapter, with FIG. 16 being taken along line 16-16 of FIG. 15.
Figure 15:
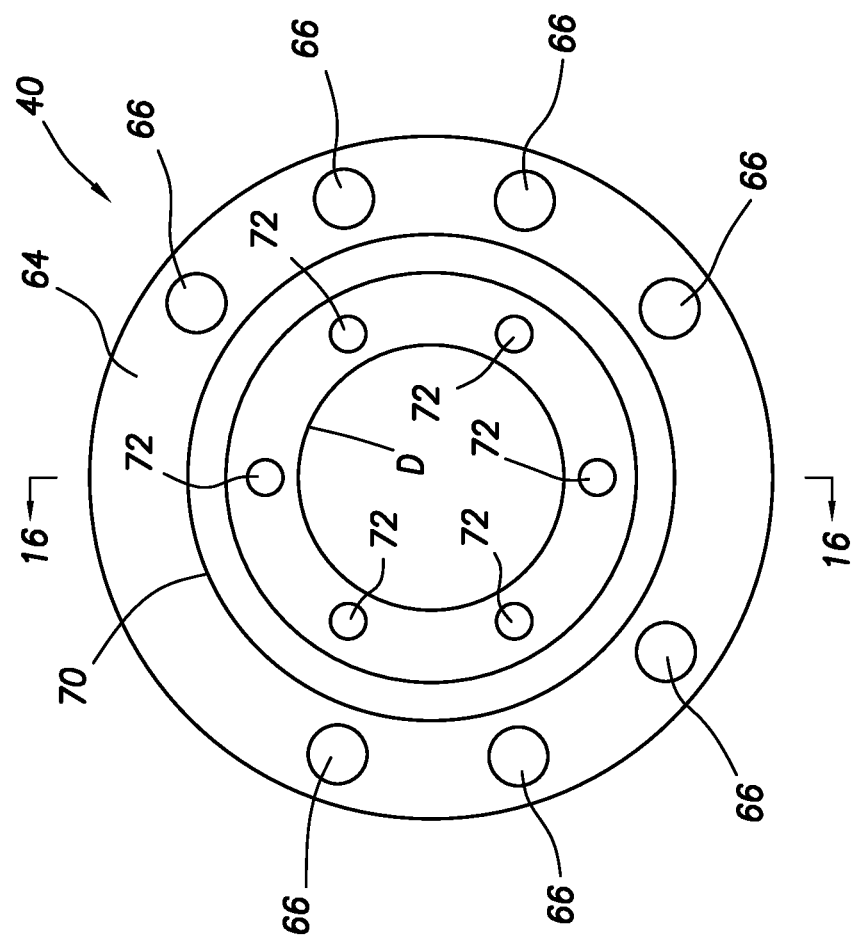

Referring additionally now to FIGS. 15 & 16, another configuration of the adapter 40 is representatively illustrated in side and cross-sectional views. In this example, a recess 76 is provided in the adapter 40, thereby shortening the adapter mounting holes 72. In addition, note that the thickness T is greater than that depicted for the FIG. 13 configuration. The recess 76 can permit the hub body 24a to be received partially in the adapter 40 when the thickness T is increased substantially.

When used in the suspension 12, the knuckle assembly 48 (including the adapter 40 configurations of FIGS. 9-16) can provide for use of a variety of different bolt-on brake components. The adapter 40 can be supplied with different mounting holes 66 (e.g., different numbers, different hole diameters, different pitches or bolt circle diameters, etc.) and different widths or thicknesses T as needed to accommodate the different brake components. Thus, the same spindle 20, bearings 22 and hub body 24a can be used with different suspension capacities, even though bolt-on brake components differ for the respective different suspension capacities.

Note that several standardized brake mount hole patterns exist in the industry, in which brake mounting fasteners that engage holes 66 are on different brake fastener pitch diameters. Similarly, these different brake assemblies may require different brake pilot diameters 70. These hole patterns may not conveniently overlay onto the same knuckle backbone 50. Additionally, clearance required for cam tubes of the lower capacity (e.g., 8 k) brake assemblies often eclipses the required brake fastener mounting holes 66 of higher capacity (e.g., 13 k) brake assemblies, thereby making it desirable, in this example, to have a knuckle backbone 50 that is narrow in width (see FIG. 8) and provided with separate unique brake adapters 40 for the different capacities.

Vehicle Suspension, System and Method Examples

In some examples, 8 k and 10 k capacity wheels 34 and brake components can be mounted to 13 k capacity spindle 20 and bearings 22.

In some examples, a common knuckle assembly 48 (including spindle 20) can be used with several different brake assemblies, wheels, etc.

In some examples, a common two-piece hub 24 can be used with different brake mounting configurations.

In some examples, a common hub 24 can be machined differently (e.g., to produce a particular wheel mounting configuration, or to accommodate a particular brake configuration), depending on the capacity of the suspension 12 in which it is to be used.

In some examples, a common two-piece hub 24 can be provided with different wheel mounting flanges 24b.

In some examples, a flange adapter 40 may be used with a common hub 24 to enable use of the common hub in different suspension 12 capacity configurations.

In some examples, a common hub 24 can be drilled for different numbers of wheel mounting studs (e.g., 6, 8 or 10 studs), and a different adapter/spacer 40 can be used for each of several corresponding different suspension 12 capacities.

In some examples, the flange adapter 40 may not be used. In these examples, another adapter or spacer could be used to space the brake shoes 26 away from the backing plate 32, or no adapter may be used at all.

It may now be appreciated that the above disclosure provides significant advancements to the arts of designing, manufacturing, assembling and maintaining vehicle suspensions. In examples described above, a same spindle 20, bearings 22 and hub body 24a can be used with a variety of differently configured wheels 34 and brake components. Different wheel mounting flanges 24b can be provided for accommodating respective different capacity wheels, and different adapters 40 can be provided for accommodating respective different capacity brake components.

The above disclosure provides to the art a vehicle suspension 12. In one example, the suspension 12 can include an adapter mounting face 58, a spindle 20 rigidly mounted relative to the adapter mounting face 58, a wheel mounting hub 24 including a hub body 24a rotatably mounted on the spindle 20 by bearings 22, and an adapter 40 that spaces a brake component away from the adapter mounting face 58. The brake component may comprise a brake backing plate 32.

A wheel mounting flange 24b may be integrally formed as part of the wheel mounting hub 24. The wheel mounting flange 24b may be separately formed from a body 24a of the wheel mounting hub.

The spindle 20 may be rigidly mounted to a steering knuckle backbone 50. The adapter mounting face 58 may be formed on the steering knuckle backbone 50.

The above disclosure also provides to the art a vehicle suspension 12 comprising a spindle 20, bearings 22, and a wheel mounting hub 24 rotatably mounted on the spindle 20 by the bearings 22. The wheel mounting hub 24 can comprise a hub body 24a and a wheel mounting flange 24b, the hub body 24a and the wheel mounting flange 24b being separate components of the wheel mounting hub 24.

The vehicle suspension 12 may also include an adapter mounting face 58, and an adapter 40 that spaces a brake component away from the adapter mounting face 58. The spindle 20 may be rigidly mounted relative to the adapter mounting face 58. The brake component can comprise a brake backing plate 32.

A system for adapting a vehicle suspension 12 to different suspension capacities is also described above. In one example, the system can comprise a spindle 20, bearings 22, and multiple wheel mounting hubs 24 configured to be rotatably mounted on the spindle 20 by the bearings 22. The wheel mounting hubs 24 can including a same hub body 24a configuration (e.g., at interfaces between the hub body 24a, the spindle 20 and the bearings 22) configured to be rotatably mounted on the spindle 20 by the bearings 22, but the wheel mounting hubs 24 include respective different wheel mounting flanges 24b.

The system can also include an adapter mounting face 58, and an adapter 40 that spaces a brake component away from the adapter mounting face 58.

The wheel mounting flanges 24b may be integrally formed as parts of the respective wheel mounting hubs 24. The wheel mounting flanges 24b may ne separately formed from the respective hub bodies 24a.

The spindle 20 may be rigidly mounted to a steering knuckle backbone 50. An adapter mounting face 58 may be formed on the steering knuckle backbone 50. The system can include multiple brake mounting adapters 40 configured to space a brake component away from the adapter mounting face 58, the brake mounting adapters 40 having respective different thicknesses T.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

In the above description of the representative examples, directional terms (such as "above," "below," "upper," "lower," etc.) are used for convenience in referring to the accompanying drawings. However, it should be clearly understood that the scope of this disclosure is not limited to any particular directions described herein.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A vehicle suspension, comprising:
   an adapter mounting face;
   a spindle rigidly mounted relative to the adapter mounting face;
   a wheel mounting hub including a hub body rotatably mounted on the spindle by bearings; and
   multiple adapters, each of the adapters being configured to space a brake component away from the adapter mounting face, and each of the adapters corresponding to a respective different suspension capacity when used with the same spindle, hub body, and bearings.

2. The vehicle suspension of claim 1, in which the brake component comprises a brake backing plate.

3. The vehicle suspension of claim 1, in which a wheel mounting flange is integrally formed as part of the wheel mounting hub.

4. The vehicle suspension of claim 1, in which a wheel mounting flange is separately formed from the hub body of the wheel mounting hub.

5. The vehicle suspension of claim 1, in which the spindle is rigidly mounted to a steering knuckle backbone.

6. The vehicle suspension of claim 5, in which the adapter mounting face is formed on the steering knuckle backbone.

7. A vehicle suspension, comprising:
a spindle rigidly mounted to a steering knuckle;
bearings; and
a wheel mounting hub rotatably mounted on the spindle by the bearings, the wheel mounting hub comprising a hub body and a wheel mounting flange, the hub body and the wheel mounting flange being separate components of the wheel mounting hub, thereby permitting replacement of the wheel mounting flange with a different wheel mounting flange associated with a different suspension capacity using the same spindle, hub body, and bearings.

8. The vehicle suspension of claim 7, further comprising:
an adapter mounting face; and
an adapter that spaces a brake component away from the adapter mounting face.

9. The vehicle suspension of claim 8, in which the spindle is rigidly mounted relative to the adapter mounting face.

10. The vehicle suspension of claim 8, in which the brake component comprises a brake backing plate.

11. The vehicle suspension of claim 8, in which the adapter mounting face is formed on the steering knuckle.

12. A system for adapting a vehicle suspension to different suspension capacities, the system comprising:
a spindle rigidly mounted to a steering knuckle;
bearings; and
multiple wheel mounting hubs, in which each wheel mounting hub is configured to be rotatably mounted on the spindle by the bearings, the wheel mounting hubs including a same hub body internal configuration configured to be rotatably mounted on the spindle by the bearings, but the wheel mounting hubs including respective different wheel mounting flanges.

13. The system of claim 12, further comprising:
an adapter mounting face; and
an adapter that spaces a brake component away from the adapter mounting face.

14. The system of claim 13, in which the brake component comprises a brake backing plate.

15. The system of claim 12, in which the wheel mounting flanges are integrally formed as parts of the respective wheel mounting hubs.

16. The system of claim 12, in which the wheel mounting flanges are separately formed from the respective hub bodies.

17. The system of claim 12, in which an adapter mounting face is formed on the steering knuckle.

18. The system of claim 17, further comprising multiple brake mounting adapters, in which each brake mounting adapter is configured to space a brake component away from the adapter mounting face, the brake mounting adapters having respective different thicknesses.

* * * * *